United States Patent
Mizuno

(10) Patent No.: US 8,101,753 B2
(45) Date of Patent: Jan. 24, 2012

(54) PRODUCTION METHOD OF PYRIMIDINE COMPOUNDS

(75) Inventor: Hajime Mizuno, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 1117 days.

(21) Appl. No.: 11/577,377

(22) PCT Filed: Nov. 4, 2005

(86) PCT No.: PCT/JP2005/020678
§ 371 (c)(1),
(2), (4) Date: Apr. 17, 2007

(87) PCT Pub. No.: WO2006/051891
PCT Pub. Date: May 18, 2006

(65) Prior Publication Data
US 2008/0039445 A1 Feb. 14, 2008

(30) Foreign Application Priority Data
Nov. 12, 2004 (JP) ................... 2004-328689

(51) Int. Cl.
*C07D 239/02* (2006.01)
(52) U.S. Cl. .............. 544/322; 544/242; 544/319
(58) Field of Classification Search ............ 544/242, 544/319, 322
See application file for complete search history.

(56) References Cited

U.S. PATENT DOCUMENTS

| 2,937,171 | A | 5/1960 | Smith | |
|---|---|---|---|---|
| 5,420,255 | A | 5/1995 | Arnold et al. | |
| 6,838,463 | B2 * | 1/2005 | Mizuno et al. | 514/269 |
| 2004/0077669 | A1 | 4/2004 | Mizuno et al. | |

FOREIGN PATENT DOCUMENTS

| EP | 0295218 A1 | | 5/1988 |
|---|---|---|---|
| JP | 5-222306 A | | 8/1993 |
| JP | 2003-34682 | * | 2/2003 |
| JP | 2003-34682 A | | 2/2003 |
| JP | 2003-267957 A | | 9/2003 |
| WO | 02/24663 A2 | | 3/2002 |
| WO | WO 03/076415 A1 | | 9/2003 |
| WO | WO 2004/099160 A1 | | 11/2004 |

OTHER PUBLICATIONS

G.M. Brooke, et al. 'Partially Fluorinated Ieterocyclic Compounds. Part 22, The Preparation of Allyl 2,5,6-Trifluoropyrimidin-4-yl Ether and Related Compounds and a Study of their Claisen Rearrangement Reactions. A New Route to 5-Fluorouracil and Barbituric Acid Derivatives', Journal of the Chemical Society, Perkin Transactions 1, No. 3, (1986), pp. 515-520.

* cited by examiner

Primary Examiner — Paul V. Ward
(74) Attorney, Agent, or Firm — Sughrue Mion, PLLC

(57) ABSTRACT

4-amino-6-alkynyloxypyrimidine compounds shown by the formula (V)

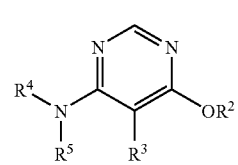

(V)

which has a controlling activity against pests can be produced by the method which comprises the first step which produces a 4-fluoro-6-alkynyloxypyrimidine compound shown by the formula (I)

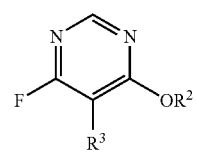

(I)

by making a 4,6-difluoropyrimidine compound shown by the formula (II) react with an alcohol compound shown by the formula (III)

H—OR² (III)

in the presence of a tertiary amine;
and the second step which produces the 4-amino-6-alkynyloxypyrimidine compound shown by the formula (V) by making the 4-fluoro-6-alkynyloxypyrimidine compound shown by the formula (I) react with an amine compound shown by the formula (IV)

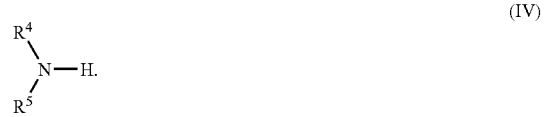

(IV)

6 Claims, No Drawings

PRODUCTION METHOD OF PYRIMIDINE COMPOUNDS

BACKGROUND OF THE INVENTION

1. Technical Field

The present invention relates a production method of 4-amino-6-alkynyloxypyrimidine compound.

2. Background Art

In WO 02/24663 A2, it is known that a certain kind of 4-amino-6-alkynyloxypyrimidine compounds has a controlling activity against pests. Furthermore, another kind of 4-amino-6-alkynyloxypyrimidine compounds also has a controlling activity against pests.

The object of the present invention is to provide a novel production method of a 4-amino-6-alkynyloxypyrimidine compound which has a controlling activity against pests and a intermediates for producing it.

SUMMARY OF THE INVENTION

The present invention provides [1] to [7] described below.
[1] A production method of a 4-amino-6-alkynyloxypyrimidine compound shown by the formula (V):

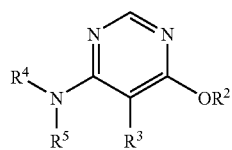

wherein $R^2$ represents C3 to C7 alkynyl, $R^3$ represents hydrogen or halogen, and $R^4$ and $R^5$ are combined together to represent C4 to C7 polymethylene and said polymethylene may be substituted by one or more groups selected from the group consisting of halogen, trifluoromethyl and C1 to C4 alkyl;
which comprises
the first step which produces a 4-fluoro-6-alkynyloxypyrimidine compound shown by the formula (I):

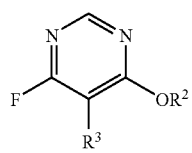

wherein $R^2$ and $R^3$ have the same meanings as described above, by making a 4,6-difluoropyrimidine compound shown by the formula (II):

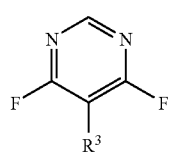

wherein $R^3$ has the same meaning as described above, react with an alcohol compound shown by the formula (III):

$$H\text{—}OR^2 \quad (III)$$

wherein $R^2$ has the same meaning as described above, in the presence of a tertiary amine;
and the second step which produces the 4-amino-6-alkynyloxypyrimidine compound shown by the formula (V) by making the 4-fluoro-6-alkynyloxypyrimidine compound shown by the formula (I) react with an amine compound shown by the formula (IV):

wherein $R^4$ and $R^5$ have the same meanings as described above (referred as the production method of the present invention hereinafter).

[2] The production method of a 4-amino-6-alkynyloxypyrimidine compound shown by the formula (V) according to [1], wherein $R^2$ is 2-butynyl, $R^3$ is fluorine, and $R^4$ and $R^5$ are combined together to represent the group of formula —CH$_2$CH(CH$_3$)CH$_2$CH(CH$_3$)CH$_2$—[

3] The production method of a 4-amino-6-alkynyloxypyrimidine compound shown by the formula (V) according to [1] or [2], wherein the tertiary amine is triethylamine.

[4] A production method of a 4-fluoro-6-alkynyloxypyrimidine compound shown by the formula (I):

wherein $R^2$ represents C3 to C7 alkynyl, and $R^3$ represents hydrogen or halogen,
which comprises
the step making a 4,6-difluoropyrimidine compound shown by the formula (II):

wherein $R^3$ has the same meaning as described above, react with an alcohol compound shown by the formula (III):

$$H\text{—}OR^2 \quad (III)$$

wherein $R^2$ has the same meaning as described above, in the presence of a tertiary amine.

[5] The production method of a 4-fluoro-6-alkynyloxypyrimidine compound shown by the formula (I) according to [4], wherein $R^2$ is 2-butynyl, and $R^3$ is fluorine.

[6] The production method of a 4-fluoro-6-alkynyloxypyrimidine compound shown by the formula (I) according to [4] or [5], wherein the tertiary amine is triethyl amine.

[7] A compound of 4-fluoro-6-alkynyloxypyrimidine compound shown by the formula (I):

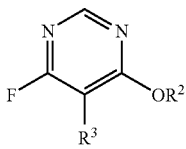

wherein $R^2$ represents C3 to C7 alkynyl, and $R^3$ represents hydrogen or halogen.

DETAILED DESCRIPTION OF THE INVENTION

The production method of the present invention comprises the first step which produces a 4-fluoro-6-alkynyloxypyrimidine compound shown by the formula (I) by making a 4,6-difluoropyrimidine compound shown by the formula (II) react with an alcohol compound shown by the formula (III) in the presence of a tertiary amine;
and the second step which produces the 4-amino-6-alkynyloxypyrimidine compound shown by the formula (V) by making the 4-fluoro-6-alkynyloxypyrimidinecompoundshown by the formula (I) react with an amine compound shown by the formula (IV).

In the present invention,
C3 to C7 alkynyl represented by $R^2$ includes, for example, 2-propynyl, 2-butynyl, 1-methyl-2-butynyl, 2-pentynyl, 4,4-dimethyl-2-pentynyl, 1-methyl-2-propynyl and 1,1-dimethyl-2-propynyl.

Halogen represented by $R^3$ includes, for example, fluorine and chlorine.

C4 to C7 polymethylene represented by $R^4$ and $R^5$ being combined together; wherein said polymethylene may be substituted by one or more group selected from the group consisting of halogen, trifluoromethyl and C1 to C4 alkyl;
includes, for example, tetramethylene, 1-methyltetramethylene, 2-methyltetramethylene, 1-ethyltetramethylene, 1-propyltetramethylene, 1-isopropyltetramethylene, 1-(tert-butyl)tetramethylene, 2-ethyltetramethylene, 1,4-dimethyltetramethylene, 2,3-dimethyltetramethylene, 2,2-dimethyltetramethylene, 2-fluorotetramethylene, 2-(trifluoromethyl)tetramethylene, pentamethylene, 1-methylpentamethylene, 2-methylpentamethylene, 3-methylpentamethylene, 1-ethylpentamethylene, 2-ethylpentamethylene, 1-propylpentamethylene, 2-propylpentamethylene, 3-propylpentamethylene, 1-isopropylpentamethylene, 2-isopropylpentamethylene, 3-isopropylpentamethylene, 1-(tert-butyl)pentamethylene, 2-(tert-butyl)pentamethylene, 3-(tert-butyl)pentamethylene, 1-(sec-butyl)pentamethylene, 2-(sec-butyl)pentamethylene, 1,5-dimethylpentamethylene, 1,3-dimethylpentamethylene, 1,4-dimethylpentamethylene, 2,4-dimethylpentamethylene, 1,1-dimethylpentamethylene, 2,2-dimethylpentamethylene, 3,3-dimethylpentamethylene, 2-ethyl-5-methylpentamethylene, 2-ethyl-4-methylpentamethylene, 2,4-diethylpentamethylene, 1,2-dimethylpentamethylene, 2,2,4-trimethylpentamethylene, 1,2,4,5-tetramethylpentamethylene, 2,2,4,4-tetramethylpentamethylene, 2-fluoropentamethylene, 3-fluoropentamethylene, 2,2-difluoropentamethylene, 3,3-difluoropentamethylene, 2-fluoro-2-methylpentamethylene, 1-(trifluoromethyl)pentamethylene, 2-(trifluoromethyl)pentamethylene, 3-(trifluoromethyl)pentamethylene, hexamethylene, 1-methylhexamethylene, 2-methylhexamethylene, 3-methylhexamethylene, 1-ethylhexamethylene, 2-ethylhexamethylene, 3-ethylhexamethylene, 1-propylhexamethylene, 2-propylhexamethylene, 3-propylhexamethylene, 1-isopropylhexamethylene, 2-isopropylhexamethylene, 3-isopropylhexamethylene, 1-(tert-butyl)hexamethylene, 1-isobutylhexamethylene, 1-(trifluoromethyl)hexamethylene, 1,4-dimethylhexamethylene, 1,5-dimethylhexamethylene, 1,6-dimethylhexamethylene, 2,5-dimethylhexamethylene, and heptamethylene.

In the 4-amino-6-alkynyloxypyrimidine compound shown by formula (V), the 4-amino-6-alkynyloxypyrimidine compound which $R^4$ and $R^5$ being combined together represent tetramethylene is described by following formula:

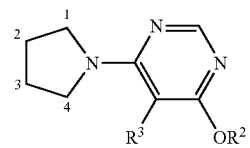

wherein $R^2$ and $R^3$ have the same meaning as described above.

In the 4-amino-6-alkynyloxypyrimidine compound shown by formula (V), the 4-amino-6-alkynyloxypyrimidine compound which $R^4$ and $R^5$ being combined together represent pentamethylene is described by following formula:

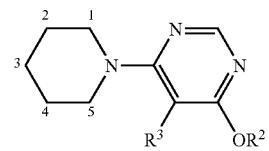

wherein $R^2$ and $R^3$ have the same meaning as described above.

In the 4-amino-6-alkynyloxypyrimidine compound shown by formula (V), the 4-amino-6-alkynyloxypyrimidine compound which $R^4$ and $R^5$ being combined together represent hexamethylene is described by following formula:

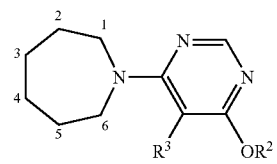

wherein $R^2$ and $R^3$ have the same meaning as described above.

In the 4-amino-6-alkynyloxypyrimidine compound shown by formula (V), the 4-amino-6-alkynyloxypyrimidine compound which $R^4$ and $R^5$ being combined together represent heptamethylene is described by following formula:

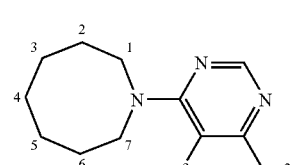

wherein $R^2$ and $R^3$ have the same meaning as described above.

The first step of the production method of the present invention is explained below.

The first step of the production method of the present invention is the step which produces a 4-fluoro-6-alkynyloxypyrimidine compound shown by the formula (I) by making a 4,6-difluoropyrimidine compound shown by the formula (II) react with an alcohol compound shown by the formula (III) in the presence of a tertiary amine.

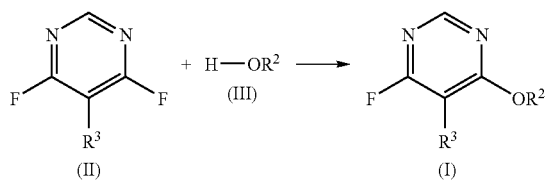

wherein $R^2$ and $R^3$ have the same meaning as described above.

The reaction of the first step of the production method of the present invention is usually carried out in the presence of a solvent.

The solvent used for the reaction includes, for example, aromatic hydrocarbons such as toluene, benzene and the like; aliphatic hydrocarbons such as hexane, octane and the like; ethers such as tetrahydrofuran, 1,4-dioxane, tert-butyl methyl ether, diethyl ether, ethylene glycol dimethyl ether, and the like; halogenated hydrocarbons such as chlorobenzene, chloroform and the like; water and the mixture thereof.

The tertiary amine used for the reaction includes, for example, triethylamine, N,N-diisopropylethylamine, 1,8-diazabicyclo[5.4.0]undec-7-ene, and 1,5-diazabicyclo[4.3.0]non-5-ene. Preferably triethylamine or N,N-diisopropylethylamine can be used.

The amount of the tertiary amine to be used for the reaction is usually 1 to 3 moles, preferably 1 to 1.5 moles, based on one mole of the 4,6-difluoropyrimidine compound shown by the formula (II).

The amount of the alcohol compound shown by the formula (III) is usually 1 to 3 moles, preferably 1 to 1.5 moles, based on one mole of the 4,6-difluoropyrimidine compound shown by the formula (II).

The reaction temperature is usually −20 to 80° C. or boiling point of the solvent. The reaction time is usually 0.1 to 24 hours, preferably 10 minutes to 8 hours.

The ending point of the reaction can be determined by analyzing reaction mixture with chromatography such as liquid chromatography, gas chromatography, thin-layer chromatography and the like.

After completion of the reaction, the 4-fluoro-6-alkynyloxypyrimidine compound shown by the formula (I) can be isolated by following procedure:

(i) the reaction mixture, as it is or after concentration, being subjected to silica gel column chromatography.

(ii) after mixing the reaction mixture with water or aqueous solution of sodium bicarbonate and the like, then adding an organic solvent if necessary, separated to two layer, and obtained organic layer being dried and concentrated.

The isolated 4-fluoro-6-alkynyloxypyrimidine compound shown by the formula (I) can be further purified by re-crystallization, chromatography and the like.

Examples of the 4-fluoro-6-alkynyloxypyrimidine compound shown by the formula (I), which can be produced by the first step of the production method of the present invention are as follows:
4,5-difluoro-6-(2-propynyloxy)pyrimidine,
4-(2-butynyloxy)-5,6-difluoropyrimidine,
4,5-difluoro-6-(2-pentynyloxy)pyrimidine,
4,5-difluoro-6-(4,4-dimethyl-2-pentynyloxy)pyrimidine,
4,5-difluoro-6-(1-methyl-2-butynyloxy)pyrimidine,
4,5-difluoro-6-(1,1-dimethyl-2-butynyloxy)pyrimidine,
4-fuluoro-6-(2-propynyloxy)pyrimidine,
4-(2-butynyloxy)-6-fluoropyrimidine,
4-fluoro-6-(2-pentynyloxy)pyrimidine,
4-(4,4-dimethyl-2-pentynyloxy)-6-fluoropyrimidine,
4-fluoro-6-(1-methyl-2-butynyloxy)pyrimidine,
4-(1,1-dimethyl-2-butynyloxy)-6-fluoropyrimidine,
5-chloro-4-fluoro-6-(2-propynyloxy)pyrimidine,
4-(2-butynyloxy)-5-chloro-6-fluoropyrimidine,
5-chloro-4-fluoro-6-(2-pentynyloxy)pyrimidine,
5-chloro-4-fluoro-6-(4,4-dimethyl-2-pentynyloxy)pyrimidine,
5-chloro-4-fluoro-6-(1-methyl-2-butynyloxy)pyrimidine and
5-chloro-4-fluoro-6-(1,1-dimethyl-2-butynyloxy)pyrimidine.

Next, the second step of the production method of the present invention is explained below.

The second step of the production method of the present invention is the step which produces the 4-amino-6-alkynyloxypyrimidine compound shown by the formula (V) by making the 4-fluoro-6-alkynyloxypyrimidine compound shown by the formula (I) react with an amine compound shown by the formula (IV).

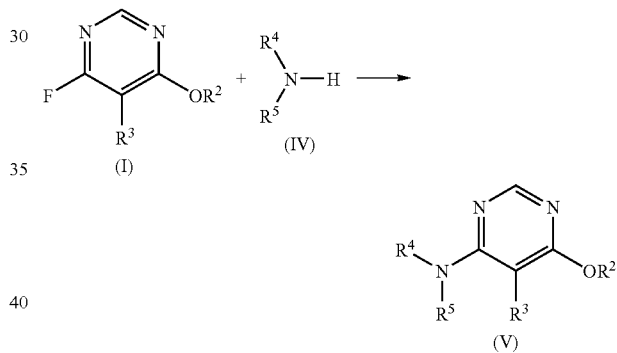

wherein $R^2$, $R^3$, $R^4$, and $R^5$ have the same meaning as described above.

The reaction of the second step of the production method of the present invention is usually carried out in the presence of a solvent.

The solvent used for the reaction includes, for example, an organic solvent including ethers such as tetrahydrofuran, diethyl ether, tert-butyl methyl ether, ethylene glycol dimethyl ether, 1,4-dioxane and the like; acid amides such as N,N-dimethylformamide and the like; nitriles such as acetonitrile and the like; sulfoxides such as dimethylsulfoxide; aliphatic hydrocarbons such as hexane and the like; aromatic hydrocarbons such as benzene, toluene and the like; and the mixture thereof; and the mixture of said organic solvent and water.

The reaction can be carried out in the presence of an inorganic base, if necessary. In that case, the amount of the inorganic base used for the reaction is usually 1 to 4 moles based on one mole of the 4-fluoro-6-alkynyloxypyrimidine compound shown by the formula (I). The inorganic base used for the reaction includes, for example, alkaline metal hydrides such as sodium hydride, potassium hydride and the like; carbonates such as potassium carbonate; alkali metal alkoxides such as potassium tert-butoxide.

The amount of the amine compound shown by the formula (IV) is usually 1 to 2 moles based on one mole of the 4-fluoro-6-alkynyloxypyrimidine compound shown by the formula (I). The amine compound shown by the formula (IV) used for the reaction can be used by the form of its salt such as hydrochloride.

The reaction temperature is usually 0 to 100° C. and the reaction time is usually 0.5 to 12 hours.

The ending point of the reaction can be determined by analyzing reaction mixture with chromatography such as liquid chromatography, gas chromatography, thin-layer chromatography and the like.

After completion of the reaction, the 4-amino-6-alkynyloxypyrimidine compound shown by the formula (V) can be isolated by following procedure:

(i) the reaction mixture, as it is or after concentration, being subjected to silica gel column chromatography.

(ii) after mixing the reaction mixture with water or aqueous solution of sodium bicarbonate and the like, then adding an organic solvent if necessary, separated to two layer, and obtained organic layer being dried and concentrated.

The isolated 4-amino-6-alkynyloxypyrimidine compound shown by the formula (V) can be further purified by re-crystallization, chromatography and the like.

Examples of the 4-amino-6-alkynyloxypyrimidine compound shown by the formula (V), which can be produced by the second step of the production method of the present invention are as follows: 4-(2-butynyloxy)-5-fluoro-6-(3,3-dimethylpyrrolidine-1-yl)pyrimidine, 4-(2-butynyloxy)-5-fluoro-6-pyrrolidinopyrimidine, 4-(2-butynyloxy)-5-fluoro-6-piperidinopyrimidine, hexahydro-1-{(4-(2-butynyloxy)-5-fluoro-6-pyrimidinyl}azepine, 5-fluoro-4-(2-pentynyloxy)-6-pyrrolidinopyrimidine, 5-fluoro-4-(2-pentynyloxy)-6-piperidinopyrimidine, hexahydro-1-{5-fluoro-6-(2-pentynyloxy)-4-pyrimidinyl}azepine, 4-(2-butynyloxy)-5-fluoro-6-(3,5-dimethylpiperidino)pyrimidine, 1-(6-(2-butynyloxy)pyrimidine-4-yl)-cis-2,6-dimethylhexahydroazepine and 4-(2-butynyloxy)-6-(3-trifluoromethylpiperidino)pyrimidine.

Furthermore, the compounds which is used for the production method of the present invention are described.

Reference Production Method A

The amine compound shown by the formula (IV'), in the compound shown by the formula (IV), can be produced, for example, according to following scheme.

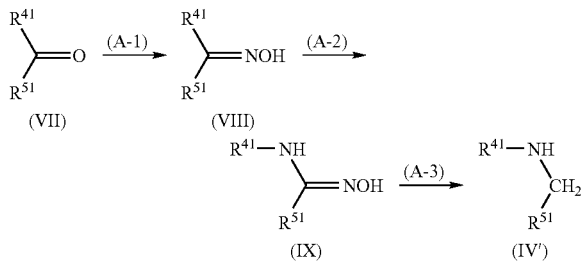

wherein $R^{41}$ and $R^{51}$ are combined together to represent C3 to C6 polymethylene and said polymethylene may be substituted by one or more group selected from the group consisting of halogen, trifluoromethyl and C1 to C4 alkyl.

Step (A-1)

The compound shown by the formula (VIII) can be produced by making the compound shown by the formula (VII) react with hydroxylamine or its salt such as hydrochloride.

The reaction is usually carried out in the presence of a solvent.

The solvent used for the reaction includes, for example, ethers such as tetrahydrofuran, diethyl ether and the like; acid amides such as N,N-dimethylformamide and the like; alcohols such as methanol, ethanol and the like; water and the mixture thereof.

The base used for the reaction includes, for example, inorganic bases such as sodium hydroxide, potassium hydroxide and the like; tertiary amines such as triethylamine and the like; nitrogen containing aromatics such as pyridine and the like.

The amount of hydroxylamine or its salt is usually 1 to 3 moles based on the compound shown by the formula (VII) and that to the base is usually 1 to 5 moles.

The reaction temperature is usually 0 to 80° C., and the reaction time is usually 1 to 24 hours.

After completion of the reaction, the compound shown by the formula (VIII) can be isolated by the procedure such as extracting the reaction mixture with an organic solvent, drying and concentrating. The isolated compound of the formula (VIII) can be further purified by chromatography and the like.

The compound shown by the formula (IX) is, for example, a compound described in Synthesis, (1980), p. 222-223 or J. Am. Chem. Soc., (1983), 105, p. 2381-2843. Or it can be produced by the procedure described as following.

Step (A-2)

The compound shown by the formula (IX) can be produced by making Beckmann rearrangement of the compound shown by the formula (VIII).

The reaction is usually carried out in the presence of a solvent.

The solvent used for the reaction includes, for example, acid amides such as N,N-dimethylformamide; aromatic hydrocarbons such as toluene, benzene and the like; and the mixture thereof.

The Beckmann rearrangement reaction is usually carried out in the presence of chlorinating agent such as phosphorus oxychloride, thionyl chloride; polyphosphoric acid; sulfuric acid or the like.

The amount of chlorinating agent, polyphosphoric acid, sulfuric acid or the like used for the reaction is usually 0.1 moles to excess amount based on one mole of the compound shown by the formula (VIII).

The reaction temperature is usually 0 to 140° C., and the reaction time is usually 1 to 24 hours.

After completion of the reaction, the compound shown by the formula (IX) can be isolated by the procedure such as extracting the reaction mixture with an organic solvent, drying and concentrating. The isolated compound of the formula (IX) can be further purified by chromatography and the like.

The compound shown by the formula (IV') can be produced, for example, by the procedure described below.

Step (A-3)

The compound shown by the formula (IV') can be produced by making the compound shown by the formula (IX) react with reducing agent.

The reaction is usually carried out in the presence of a solvent.

The solvent used for the reaction includes, for example, ethers such as tetrahydrofuran, diethyl ether and the like.

The reducing agent used for the reaction includes, for example, aluminum hydrides such as lithium aluminum hydride and the like.

The amount of the reducing agent used for the reaction is usually 0.5 to 6 moles based on one mole of the compound shown by the formula (IX).

The reaction temperature is usually 0 to 120° C., and the reaction time is usually 1 to 24 hours.

After completion of the reaction, the compound shown by the formula (IV') can be isolated by following procedure.

(i) the following method; small amount of water and small amount of aqueous solution of sodium hydroxide were added to the reaction mixture and stirred, dried, then if necessary distilled.

(ii) the following method; small amount of water and small amount of aqueous solution of sodium hydroxide were added to the reaction mixture and stirred, dried, then the mixture is stirred in the presence of a hydrogen chloride or its solution in the presence or absence of a solvent, then concentrated to obtain a hydrochloride of the compound shown by the formula (IV').

The compound shown by the formula (IV') includes, for example, the compound described in J. Am. Chem. Soc., (1983), 105, p. 2381-2843 or J. Heterocyclic. Chem., (1980) 17, p. 603. And they can be produced by the method described in said literature.

Reference Production Method B

The compound shown by the formula (IV"), in the compound shown by the formula (IV), can be produced, for example, from the compound shown by the formula (X) according to following scheme.

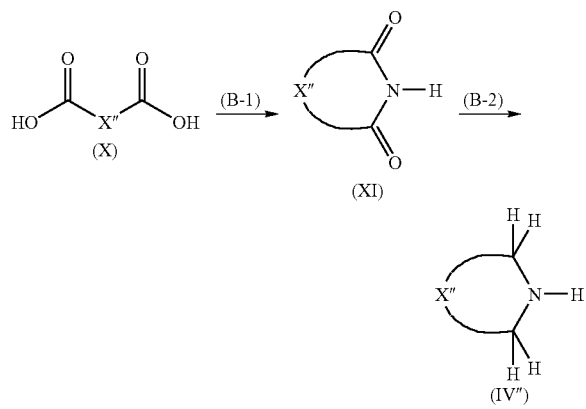

wherein

X" represents C2 to C5 polymethylene and said polymethylene may be substituted by one or more groups selected from the group consisting of halogen, trifluoromethyl and C1 to C4 alkyl.

Step (B-1)

The compound shown by the formula (XI) can be produced by making the compound shown by the formula (X) react with urea.

The reaction is usually carried out in the absence of a solvent.

The amount of the urea used for the reaction in usually 10 moles to excess amount based on one mole of the compound shown by the formula (X).

The reaction temperature is usually 50 to 170° C., and the reaction time is usually 1 to 24 hours.

After completion of the reaction, the compound shown by the formula (IX) can be isolated by the procedure such as extracting with an organic solvent, drying and concentrating. The isolated compound of the formula (XI) can be further purified by chromatography and the like.

Step (B-2)

The compound shown by the formula (IV') can be produced by making the compound shown by the formula (IX) react with reducing agent.

The reaction is usually carried out in the presence of a solvent.

The solvent used for the reaction includes, for example, ethers such as tetrahydrofuran, diethyl ether and the like.

The reducing agent used for the reaction includes, for example, aluminum hydrides such as lithium aluminum hydride and the like.

The amount of the reducing agent used for the reaction is usually 1 to 6 moles based on one mole of the compound shown by the formula (XI).

The reaction temperature is usually 0 to 120° C., and the reaction time is usually 1 to 24 hours.

After completion of the reaction, the compound shown by the formula (IV") can be isolated by following procedure.

(i) the following method; small amount of water and small amount of aqueous solution of sodium hydroxide were added to the reaction mixture and stirred, dried, then if necessary distilled.

(ii) the following method; small amount of water and small amount of aqueous solution of sodium hydroxide were added to the reaction mixture and stirred, dried, then the mixture is stirred in the presence of a hydrogen chloride or its solution in the presence or absence of a solvent, then concentrated to obtain a hydrochloride of the compound shown by the formula (IV").

The 4-fluoro-6-alkynyloxypyrimidine compound shown by the formula (I) and alcohol compound shown by the formula (III) are known compounds or can be produced in a same manner as known method.

The 4-amino-6-alkynyloxypyrimidine compound shown by the formula (V) produced by the production method of the present invention have an pesticidal activity. The pests against which the 4-amino-6-alkynyloxypyrimidine compound shown by the formula (V) include arthropods (e.g., insects, acarines) and nemathelminthes, specific examples of which are as follows:

Hemiptera:

Delphacidae such as *Laodelphax striatellus*, *Nilaparvata lugens*, and *Sogatella furcifera*, Deltocephalidae such as *Nephotettix cincticeps* and *Empoasca onukii*, Aphididae such as *Aphis gossypii* and *Myzus persicae*, Pentatomidae, Aleyrodidae such as *Trialeurodes vaporariorum*, *Bemisia tabaci*, and *Bemisia argentifolii*, Coccidae, Tingidae, Psyllidae, etc.

Lepidoptera:

Pyralidae such as *Chilo suppressalis, Cnaphalocrocis medinalis, Ostrinia nubilalis*, and *Parapediasia teterrella*, Noctuidae such as *Spodoptera litura, Spodoptera exigua, Pseudaletia separata, Mamestra brassicae, Agrotis ipsilon, Trichoplusia* spp., *Heliothis* spp., *Helicoverpa* spp., and *Earias* spp., Pieridae such as *Pieris rapae crucivora*, Tortricidae such as *Adoxophyes orana fasciata, Grapholita molesta*, and *Cydia pomonella*, Carposimidae such as *Carposina niponensis*, Lyonetiidae such as *Lyonetia clerkella*, Gracillariidae such as *Phyllonorycter ringoniella*, Phyllocnistidae such as *Phyllocnistis citrella*, Yponomeutidae such as *Plutella xylostella*, Gelechiidae such as *Pectinophora gossypiella*, Arctiidae, Tineidae, etc.

Diptera:

Calicidae such as *Culex pipiens pallens, Culex tritaeniorhynchus*, and *Culex quinquefasciatus, Aedes* spp. such as *Aedes aegypti* and *Aedes albopictus, Anopheles* spp. such as *Anopheles sinensis*, Chironomidae, Muscidae such as *Musca domestica* and *Muscina stabulans*, Calliphoridae, Sarcophagidae, Anthomyiidae, Cecidomyiidae such as *Delia platura* and *Delia antiqua*, Tephritidae, Drosophilidae, Psychodidae, Tabanidae, Simuliidae, Stomoxyidae, Agromyzidae, etc.

Coleoptera:

*Diabrotica* spp. such as *Diabrotica virgifera virgifera* and *Diabrotica undecimpunctata howardi*, Scarabaeidae such as *Anomala cuprea* and *Anomala rufocuprea*, Curculionidae such as *Sitophilus zeamais, Lissorhoptrus oryzophilus*, and *Callosobruchuys chienensis*, Tenebrionidae such as *Tenebrio molitor* and *Tribolium castaneum*, Chrysomelidae such as *Oulema oryzae, Aulacophora femoralis, Phyllotreta striolata*, and *Leptinotarsa decemlineata*, Anobiidae, *Epilachna* spp. such as *Epilachna vigintioctopunctata*, Lyctidae, Bostrychidae, Cerambycidae, *Paederus fuscipes*, etc.

Thysanoptera:

Thripidae such as *Thrips* spp., e.g., *Thrips palmi, Frankliniella* spp., e.g., *Frankliniella occidentalis*, and *Sciltothrips* spp., e.g., *Sciltothrips dorsalis*, and Phlaeotheripidae, etc.

Hymenoptera:

Tenthredimidae, Formicidae, Vespidae, etc.

Dictyoptera:

Blattidae, Blattellidae, etc.

Orthoptera:

Acrididae, Gryllotalpidae, etc.

Aphaniptera:

*Purex irritans* etc.

Anoplura:

*Pediculus humanus capitis* etc.

Isoptera:

Termitidae etc.

Acarina:

Tetranychidae such as *Tetranychus urticae, Tetranychus kanzawai, Panonychus citri, Panonychus ulmi*, and *Oligonychus*, Eriophyidae such as *Aculops pelekassi* and *Aculus schlechtendali*, Tarsonemidae such as *Polyphagotarsonemus latus*, Tenuipalpidae, Tuckerellidae, Ixodidae such as *Haemaphysalis longicornis, Haemaphysalis flava, Dermacentor taiwanicus, Ixodes ovatus, Ixodes persulcatus*, and *Boophilus microplus*, Acaridae such as *Tyrophagus putrescentiae*, Epidermoptidae such as *Dermatophagoides farinae* and *Dermatophagoides ptrenyssnus*, Cheyletidae such as *Cheyletus eruditus, Cheyletus malaccensis* and *Cheyletus moorei Dermanyssus* spp., etc.

Nematodes:

*Pratylenchus coffeae, Pratylenchus fallax, Heterodera glycines, Globadera rostochiensis, Meloidogyne hapla, Meloidogyne incognita*, etc.

When the 4-amino-6-alkynyloxypyrimidine compounds shown by the formula (V) are used as an active ingredient of pesticides, the 4-amino-6-alkynyloxypyrimidine compounds shown by the formula (V) may be used as such; however, the 4-amino-6-alkynyloxypyrimidine compounds shown by the formula (V) are usually used after formulation into oil sprays, emulsifiable concentrates, flowables, granules, dusts, poison baits, or microcapsules, by mixing with solid carriers, liquid carriers, gaseous carriers, and/or baits, and if necessary, by addition of surfactants or other auxiliaries and processing. These formulations may usually contain the 4-amino-6-alkynyloxypyrimidine compounds shown by the formula (V) in 0.01% to 95% by weight.

The solid carrier used in the formulation may include fine powder or granules of clay materials such as kaolin clay, diatomaceous earth, synthetic hydrated silicon oxide, bentonite, Fubasami clay, and acid clay; various kinds of talc, ceramics, and other inorganic minerals such as sericite, quartz, sulfur, activated charcoal, calcium carbonate, and hydrated silica; and chemical fertilizers such as ammonium sulfate, ammonium phosphate, ammonium nitrate, urea, and ammonium chloride.

The liquid carrier may include water; alcohols such as methanol and ethanol; ketones such as acetone and methyl ethyl ketone; aromatic hydrocarbons such as benzene, toluene, xylene, ethylbenzene, and methylnaphthalene; aliphatic hydrocarbons such as hexane, cyclohexane, kerosene, and light oil; esters such as ethyl acetate and butyl acetate; nitriles such as acetonitrile and isobutyronitrile; ethers such as diisopropyl ether and dioxane; acid amides such as N,N-dimethylformamide and N,N-dimethylacetamide; halogenated hydrocarbons such as dichloromethane, trichloroethane, and carbon tetrachloride; dimethyl sulfoxide; and vegetable oils such as soybean oil and cottonseed oil.

The gaseous carrier or propellant may include Freon gas, butane gas, LPG (liquefied petroleum gas), dimethyl ether, and carbon dioxide.

The surfactant may include alkyl sulfate salts, alkyl sulfonate salts, alkyl arylsulfonate salts, alkyl aryl ethers and their polyoxyethylene derivatives, polyethylene glycol ethers, polyhydric alcohol esters, and sugar alcohol derivatives.

The auxiliaries may include fixing agents, dispersing agents, and stabilizers, specific examples of which are casein, gelatin, polysaccharides such as starch, gum arabic, cellulose derivatives, and alginic acid; lignin derivatives, bentonite, sugars, synthetic water-soluble polymers such as polyvinyl alcohol, polyvinyl pyrrolidone, and polyacrylic acid; PAP (isopropyl acid phosphate), BHT (2,6-di-tert-butyl-4-methylphenol), BHA (mixtures of 2-tert-butyl-4-methoxyphenol and 3-tert-butyl-4-methoxyphenol), vegetable oils, mineral oils, and fatty acids and their esters.

The base material for poison baits may include bait materials such as grain powder, vegetable oils, sugars, and crystalline cellulose; antioxidants such as dibutylhydroxytoluene and nordihydroguaiaretic acid; preservatives such as dehydroacetic acid; accidental ingestion-preventing agents such as red pepper powder; pest attractant flavors such as cheese flavor, onion flavor, and peanut oil.

The pest controlling method by using the 4-amino-6-alkynyloxypyrimidine compounds shown by the formula (V) is usually carried out by applying the pest controlling composition containing the 4-amino-6-alkynyloxypyrimidine compounds shown by the formula (V) to pests or habitats of pests.

When the pest controlling compositions containing the 4-amino-6-alkynyloxypyrimidine compounds shown by the formula (V) are used to control pests in the agriculture and forestry field, their application amounts are usually 0.1 to 10,000 g in amounts of the 4-amino-6-alkynyloxypyrimidine compounds shown by the formula (V) per 1,000 m$^2$. For emulsifiable concentrates, wettable powders, flowables, or microcapsules, these formulations are usually applied after water dilution so that the concentrations of active ingredients come to 10 to 10000 ppm, and for granules or dusts, these formulations are usually applied as such.

The pest controlling compositions containing the 4-amino-6-alkynyloxypyrimidine compounds shown by the formula (v) may be used in the foliar treatment of plants such as crop plants to be protected against pests, or may be applied to the nursery beds before planting of crop plant seedlings or to the planting holes or the bases of plants at the time of planting. For the purpose of controlling pests inhabiting the soil of a cultivated land, they may be applied to the soil. In addition, resin formulations processed into a sheet, string or other shapes may be applied by directly winding around crop plants, extending in the neighborhood of crop plants, or laying on the soil surface at the bases of plants.

Furthermore, the pest controlling composition containing the 4-amino-6-alkynyloxypyrimidine compounds shown by the formula (V) may be used in admixture with or separately but simultaneously with other insecticides, nematocides, acaricides, fungicides, herbicides, plant growth regulators, synergists, fertilizers, soil conditioners and animal feeds.

The insecticide, nematocide and/or acaricide which can be used may include organophosphorus compounds such as Fenitrothion, Fenthion, Pyridaphenthion, Diazinon, Chlorpyriphos, Chlorpyriphos-methyl, Acephate, Methidathion, Disulfoton, DDVP, Sulprofos, Profenofos, Cyanophos, Dioxabenzofos, Dimethoate, Phenthoate, Malathion, Trichlorfon, Azinphos-methyl, Monocrotophos, Dicrotophos, Ethion and Fosthiazate; carbamate compounds such as BPMC, Benfuracarb, Propoxur, Carbosulfan, Carbaryl, Methomyl, Ethiofencarb, Aldicarb, Oxamyl, Fenothiocarb, Thiodicarb, and Alanycarb;

pyrethroid compounds such as Etofenprox, Fenvalerate, Esfenvalerate, Fenpropathrin, Cypermethrin, alfa-Cypermethrin, Z-Cypermethrin, Permethrin, Cyhalothrin, lamda-Cyhalothrin, Cyfluthrin, beta-Cyfluthrin, Deltamethrin, Cycloprothrin, tau-Fluvalinate, Flucythrinate, Bifenthrin, Acrinathrin, Tralomethrin, Silafluofen, and Halfenprox;

neonicotinoid compounds such as Thiamethoxam, Dinotefuran, Acetamiprid, and Clothianidin; benzoylphenylurea compounds such as Chlorfluazuron, Teflubenzuron, Fulfenoxuron, and Lufenuron; benzoylhydrazide compounds such as Tebufenozide, Halofenozide, Methoxyfenozide, and Chromafenozide; thiadiazine derivatives such as Buprofezin; Nereistoxin derivatives such as Cartap, Thiocyclam, and Bensultap; chlorinated hydrocarbon compounds such as Endosulfan, gamma-BHC, and 1,1-bis(chlorophenyl)-2,2,2-trichloroethanol; formamidine derivatives such as Amitraz and Chlordimeform; thiourea derivatives such as Diafenthiuron; phenyl pyrazole compounds such as Ethiprole and Acetoprole; Chlorfenapyr, Pymetrozine, Spinosad, Indoxacarb, Pyridalyl, Pyriproxyfen, Fenoxycarb, Diofenolan, Cyromazine, Bromopropylate, Tetradifon, Quinomethionate, Propargate, Fenbutatin oxide, Hexythiazox, Etoxazole, Chlofentezine, Pyridaben, Fenpyroximate, Tebfenpyrad, Pyrimidifen, Fenazaquin, Acequinocyl, Bifenazate, Fluacrypyrim, Spirodiclofen, Spiromesifen, Milbemectin, Avermectin, Emamectin benzoate, Azadilactin [AZAD], and polynactin complexes [e.g., tetranactin, dinactin, trinactin].

EXAMPLES

Next, the present invention will hereinafter be further illustrated by examples; however, the present invention is not limited to these examples.

In the examples, $^1$H-NMR shows, unless otherwise indicated, by the value of chemical shift δ [ppm] which was measured by using tetramethylsilane as an internal standard in a deuterated chloroform solvent.

First, examples of the first step of the production method of the present invention are described.

Example 1-1

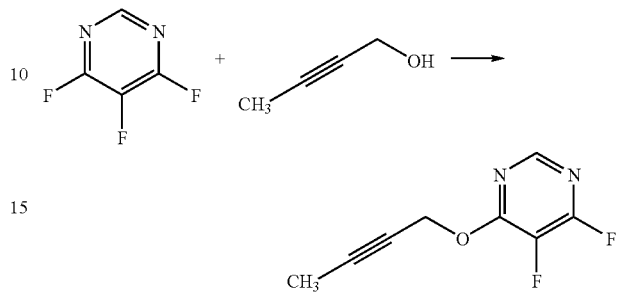

0.5 g of 4,5,6-trifluoropyrimidine, 0.31 g of 2-butyn-1-ol and 0.62 ml of triethylamine were added to 1 ml of toluene, then the mixture was stirred at room temperature for 1 hour. Then the reaction mixture was subjected to silica gel column chromatography to obtain 0.56 g of 4-(2-butynyloxy)-5,6-difluoropyrimidine.

$^1$H-NMR: 1.89 (t, 3H), 5.10 (q, 2H), 8.27 (s, 1H)

Example 1-2

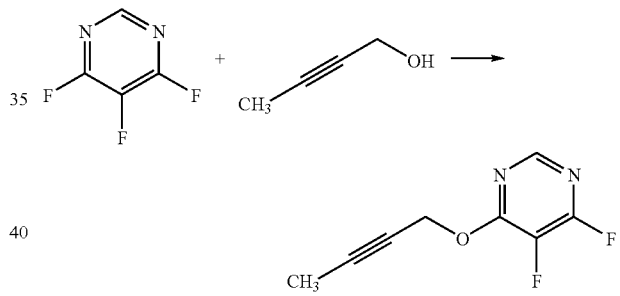

0.5 g of 4,5,6-trifluoropyrimidine, 0.31 g of 2-butyn-1-ol and 0.78 ml of N,N-diisopropylethylamine were added to 1 ml of toluene, then the mixture was stirred at room temperature for 30 minutes. Then the reaction mixture was subjected to silica gel column chromatography to obtain 0.57 g of 4-(2-butynyloxy)-5,6-difluoropyrimidine.

Example 1-3

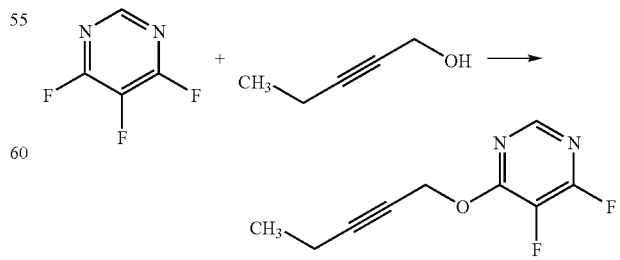

0.5 g of 4,5,6-trifluoropyrimidine, 0.38 g of 2-pentyn-1-ol and 0.62 ml of triethylamine were added to 1 ml of toluene, then the mixture was stirred at room temperature for 1 hour. Then the reaction mixture was subjected to silica gel column chromatography to obtain 0.53 g of 4,5-difluoro-6-(2-pentynyloxy)pyrimidine.

¹H-NMR: 1.15 (t, 3H), 2.26 (qt, 2H), 5.11 (t, 2H), 8.26 (s, 1H)

Example 1-4

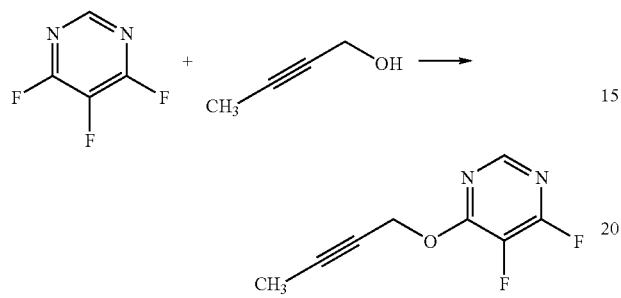

0.5 g of 4,5,6-trifluoropyrimidine, 0.31 g of 2-butyn-1-ol and 0.62 ml of N,N-diisopropylethylamine were added to 1 ml of hexane, then the mixture was stirred at room temperature for 1 hour. Then the reaction mixture was subjected to silica gel column chromatography to obtain 0.55 g of 4-(2-butynyloxy)-5,6-difluoropyrimidine.

Example 1-5

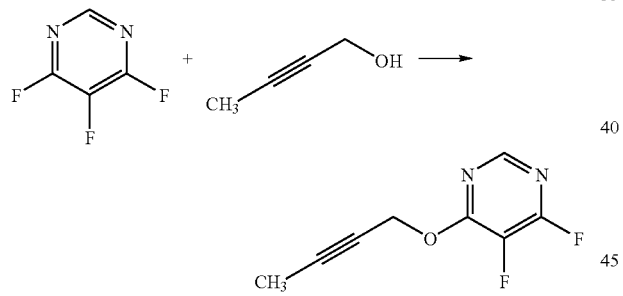

0.5 g of 4,5,6-trifluoropyrimidine, 0.31 g of 2-butyn-1-ol and 0.62 ml of N,N-diisopropylethylamine were added to 1 ml of tetrahydrofuran, then the mixture was stirred at room temperature for 1 hour. Then the reaction mixture was subjected to silica gel column chromatography to obtain 0.52 g of 4-(2-butynyloxy)-5,6-difluoropyrimidine.

Then examples of the second step of the production method of the present invention are described.

Example 2-1

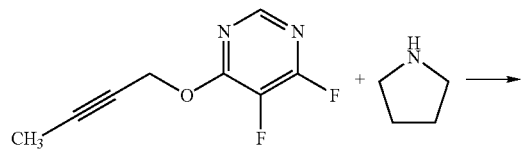

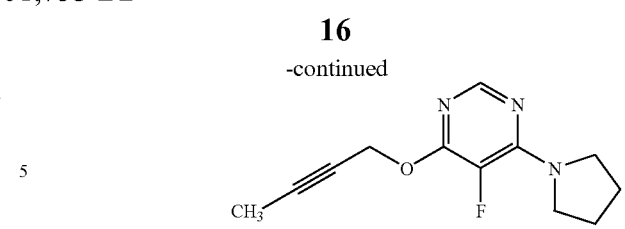

0.2 g of 4-(2-butynyloxy)-5,6-difluoropyrimidine and 0.09 g of pyrrolidine were added to 0.3 ml of toluene, then the mixture was stirred at room temperature for 3 hours. Then the reaction mixture was subjected to silica gel column chromatography to obtain 0.19 g of 4-(2-butynyloxy)-5-fluoro-6-pyrrolidinopyrimidine (referred as the present compound (1) hereinafter).

¹H-NMR: 1.88 (t, 3H), 1.90-1.98 (m, 4H), 3.64-3.68 (m, 4H), 4.97 (q, 2H), 8.02 (s, 1H)

Example 2-2

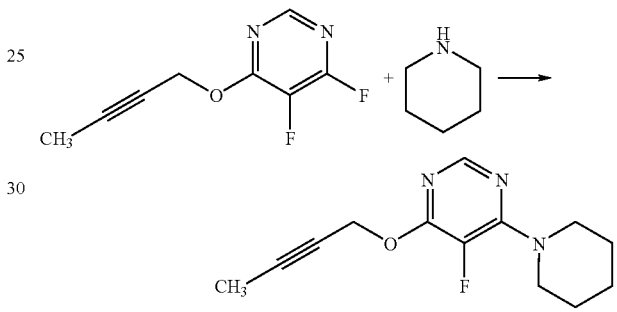

0.2 g of 4-(2-butynyloxy)-5,6-difluoropyrimidine and 0.12 g of piperidine were added to 0.3 ml of toluene, then the mixture was stirred at room temperature for 3 hours. Then the reaction mixture was subjected to silica gel column chromatography to obtain 0.25 g of 4-(2-butynyloxy)-5-fluoro-6-piperidinopyrimidine (referred as the present compound (2) hereinafter).

¹H-NMR: 1.60-1.72 (m, 6H), 1.87 (t, 3H), 3.63-3.69 (m, 4H), 4.97 (q, 2H), 8.04 (s, 1H)

Example 2-3

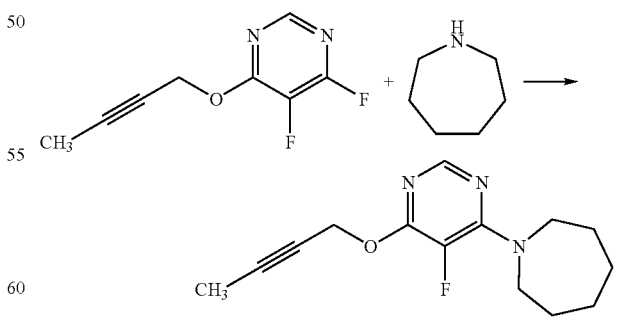

0.2 g of 4-(2-butynyloxy)-5,6-difluoropyrimidine and 0.14 g of hexamethyleneimine were added to 0.3 ml of toluene, then the mixture was stirred at room temperature for 3 hours. Then the reaction mixture was subjected to silica gel column chromatography to obtain 0.26 g of hexahydro-1-{4-(2-butynyloxy)-5-fluoro-6-pyrimidinyl}azepine (referred as the present compound (3) hereinafter).

¹H-NMR: 1.56-1.60 (m, 4H), 1.77-1.81 (m, 4H), 1.87 (t, 3H), 3.74-3.77 (m, 4H), 4.97 (q, 2H), 8.01 (s, 1H)

Example 2-4

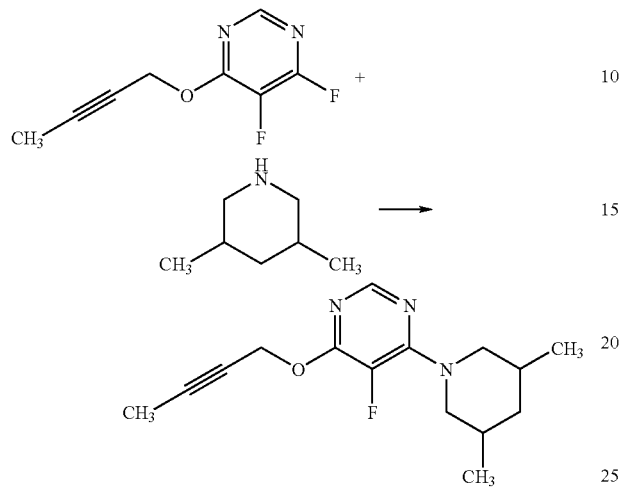

0.53 g of 4-(2-butynyloxy)-5,6-difluoropyrimidine and 0.39 g of 3,5-dimethylpiperidine (mixture of about cis:trans=7:3) were added to 1 ml of toluene, then the mixture was stirred at room temperature for 30 minutes. Then the reaction mixture was subjected to silica gel column chromatography to obtain 0.6 g of 4-(2-butynyloxy)-5-fluoro-6-(3,5-dimethylpiperidino)pyrimidine (referred as the present compound (4) hereinafter).

The present compound (4) has cis-trans isomers which are caused by relative configuration of two methyl groups on the piperidine ring. In this production example, the product which was the mixture of about cis:trans=7:3 was obtained.

Then, small portion of obtained 4-(2-butynyloxy)-5-fluoro-6-(3,5-dimethylpiperidino)pyrimidine was subjected to silica gel column chromatography to obtain cis-4-(2-butynyloxy)-5-fluoro-6-(3,5-dimethylpiperidino)pyrimidine and trans-4-(2-butynyloxy)-5-fluoro-6-(3,5-dimethylpiperidino) pyrimidine.

cis-4-(2-butynyloxy)-5-fluoro-6-(3,5-dimethylpiperidino)pyrimidine

¹H-NMR: 0.80 (dd, 1H), 0.91 (d, 6H), 1.60-1.72 (m, 2H), 1.81-1.89 (m, 4H, involving a triplet at 1.87), 2.40 (dd, 2H), 4.39 (dd, 2H), 4.97 (q, 2H), 8.03 (s, 1H)

trans-4-(2-butynyloxy)-5-fluoro-6-(3,5-dimethylpiperidino)pyrimidine

¹H-NMR: 0.94 (d, 6H), 1.49 (t, 2H), 1.87 (t, 3H), 1.94-2.03 (m, 2H), 3.31 (dd, 2H), 3.75 (dd, 2H), 4.97 (q, 2H), 8.01 (s, 1H)

Example 2-5

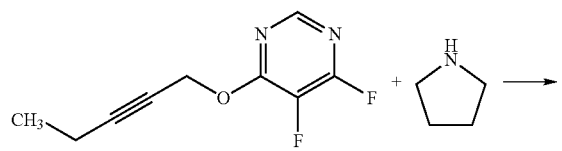

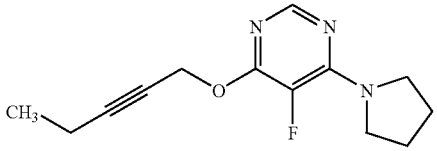

0.1 g of 4,5-difluoro-6-(2-pentynyloxy)pyrimidine and 0.04 g of pyrrolidine were added to 0.2 ml of toluene, then the reaction mixture was stirred at room temperature for 3 hours. Then the reaction mixture was subjected to silica gel column chromatography to obtain 0.11 g of 5-fluoro-4-(2-pentynyloxy)-6-pyrrolidinopyrimidine (referred as the present compound (5) hereinafter).

¹H-NMR: 1.14 (t, 3H), 1.90-1.96 (m, 4H), 2.22 (qt, 2H), 3.36-3.68 (m, 4H), 4.99 (t, 2H), 8.02 (s, 1H)

Example 2-6

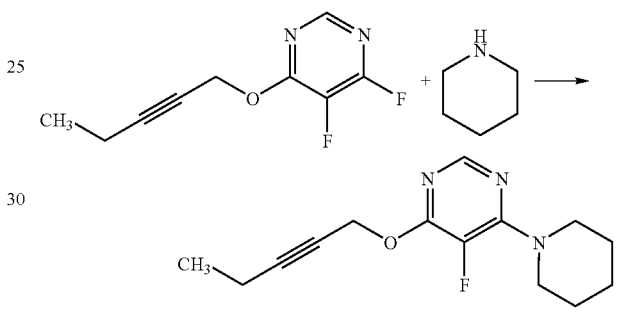

0.1 g of 4,5-difluoro-6-(2-pentynyloxy)pyrimidine and 0.05 g of piperidine were added to 0.2 ml of toluene, then the reaction mixture was stirred at room temperature for 3 hours. Then the reaction mixture was subjected to silica gel column chromatography to obtain 0.12 g of 5-fluoro-4-(2-pentynyloxy)-6-piperidinopyridine (referred as the present compound (6) hereinafter).

¹H-NMR: 1.14 (t, 3H), 1.60-1.71 (m, 6H), 2.24 (qt, 2H), 3.67-3.71 (m, 4H), 4.99 (t, 2H), 8.03 (s, 1H)

Example 2-7

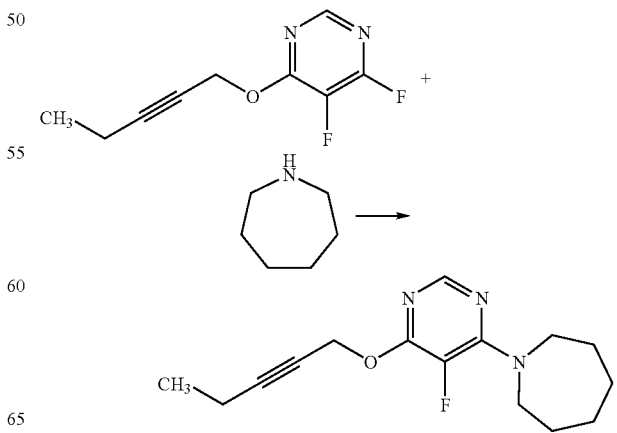

0.1 g of 4,5-difluoro-6-(2-pentynyloxy)pyrimidine and 0.06 g of hexamethyleneimine were added to 0.2 ml of toluene, then the reaction mixture was stirred at room temperature for 3 hours. Then the reaction mixture was subjected to silica gel column chromatography to obtain 0.13 g of hexahydro-1-{5-fluoro-6-(2-pentynyoxy)-4-pyrimidinyl}azepin (referred as the present compound (7) hereinafter).

$^1$H-NMR: 1.15 (t, 3H), 1.52-1.61 (m, 4H), 1.72-1.79 (m, 4H), 2.24 (qt, 2H), 3.65-3.74 (m, 4H), 4.99 (t, 2H), 8.01 (s, 1H)

Example 2-8

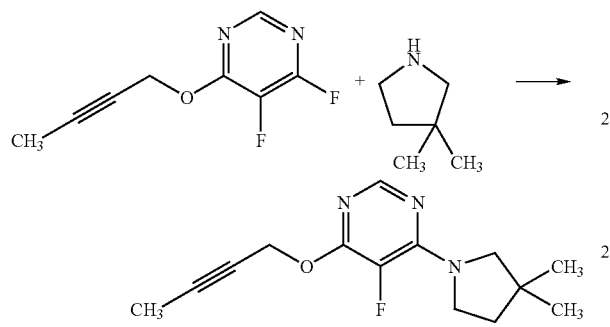

0.36 g of 4-(2-butynyloxy)-5,6-difluoropyrimidine, 0.25 g of 3,3-dimethylpyrrolidine hydrochloride and 0.62 g of potassium carbonate are added to 1 ml of acetonitrile, then the reaction mixture is stirred at 70° C. for 5 hours. Then saturated aqueous solution of ammonium chloride is added to the reaction mixture which is cooled to about room temperature, and extract with t-butyl methyl ether three times. The organic layers are joined, dried with anhydrous magnesium sulfate, and concentrated. The residue is subjected to silica gel column chromatography to obtain 4-(2-butynyloxy)-5-fluoro-6-(3,3-dimethylpyrrolidine-1-yl)pyrimidine (referred as the present compound (8) hereinafter).

Example 2-9

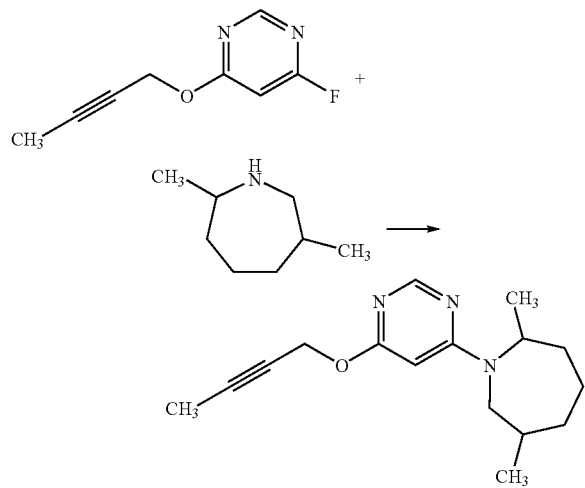

0.2 g of 4-(2-butynyloxy)-5,6-difluoropyrimidine, 0.24 g of cis-2,6-dimethylhxahydroazepin hydrochloride and 0.49 g of potassium carbonate are added to 1 ml of acetonitrile, then the reaction mixture is stirred at 70° C. for 5 hours. Then saturated aqueous solution of ammonium chloride is added to the reaction mixture which is cooled to about room temperature, and extract with t-butyl methyl ether three times. The organic layer are joined, dried with anhydrous magnesium sulfate, and concentrated. The residue is subjected to silica gel column chromatography to obtain 1-(6-(2-butynyloxy)pyrimidine-4-yl)-cis-2,6-dimethylhexahydroazepin (referred as the present compound (9) hereinafter).

Example 2-10

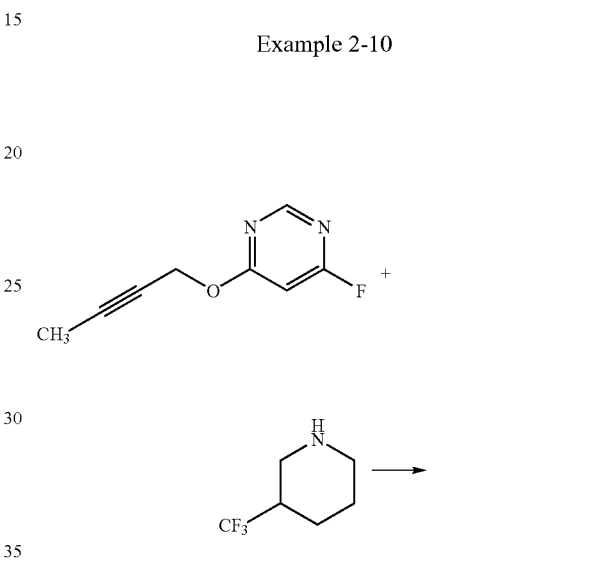

0.2 g of 4-(2-butynyloxy)-6-fluoropyrimidine and 0.15 g of 3-trifluoromethylpiperidine are added to 1 ml of toluene, then the mixture is stirred at room temperature for 30 minutes. Then the reaction mixture is subjected to silica gel column chromatography to obtain 4-(2-butynyloxy)-6-(3-trifluoromethylpyperidino)pyrimidine (referred as the present compound (10) hereinafter).

Next, the production methods of the amine compound shown by the formula (IV) are described as Reference Production Example.

Reference Production Example 3-1

10 g of 3,3-dimethyl succinic acid and 102.7 g of urea were mixed and stirred at 160° C. for 10 hours. Then water was added to the reaction mixture which was cooled to about 100° C., and further cooled to about room temperature, then extracted with ethyl acetated three times. The organic layers were joined, washed with saturated aqueous solution of sodium chloride, dried with anhydrous magnesium sulfate, and concentrated. The residue was subjected to silica gel column chromatography to obtain 7.8 g of 3,3-dimethyl-2,5-pyrrolidine dion.

3,3-dimethyl-2,5-pyrrolidine dion

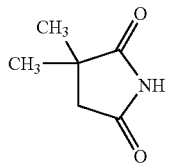

$^1$H-NMR: 1.35 (s, 6H), 2.60 (s, 2H), 8.36 (br, 1H)

Reference Production Example 3-2

0.96 g of lithium aluminum hydride was suspended to 15 ml of tetrahydrofuran, and 1 g of 3,3-dimethyl-2,5-pyrrolidine dion was slowly added to the suspension at 0° C., then it was refluxed for 12 hours. After the reaction mixture was cooled to 0° C., 0.96 ml of water, 0.96 ml of 15% of aqueous solution of sodium hydroxide and 2.88 ml of water were added successively to it, then the mixture was stirred for 30 minutes. Anhydrous magnesium sulfate was added to it and filtered through Celite®. 15.74 ml of hydrogen chloride-diethyl ether solution (1 mol/L) was added to the obtained filtrate at 0° C., and stirred for 1 hour. The mixture was concentrated to obtain 0.45 g of 3,3-dimethylpyrrolidine hydrochloride.

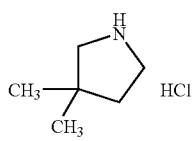

$^1$H-NMR: 1.19 (s, 6H), 1.79-1.84 (m, 2H), 3.01-3.07 (m, 2H), 3.43-3.51 (m, 2H), 9.37 (br, 2H)

Reference Production Example 3-3

5 g of 2,6-dimethylcyclohexanone and 5.51 g of hydroxylamine hydrochloride were suspended to 80 ml of ethanol, then 9.4 g of pyridine was dropped at 0° C. The mixture was stirred at room temperature for 4 hours, then the reaction mixture was concentrated. Water was added to the residue and extracted with ethyl acetate three times. The organic layers were joined, washed with saturated aqueous solution of sodium chloride, dried with anhydrous magnesium sulfate, and concentrated. The residue was subjected to silica gel column chromatography to obtain 3.1 g of cis-2,6-dimethylcyclohexanoneoxime and 1.3 g of trans-2,6-dimethylcyclohexanoneoxime.

cis-2,6-dimethylcyclohexanoneoxime

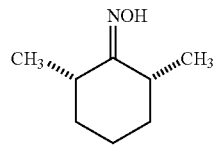

$^1$H-NMR: 1.19 (d, 3H), 1.21 (d, 3H), 1.42-1.51 (m, 1H), 1.53-1.85 (m, 5H), 2.58-2.67 (m, 1H), 3.39-3.48 (m, 1H), 8.58 (brs, 1H)

trans-2,6-dimethylcyclohexanoneoxime

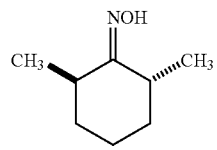

$^1$H-NMR: 1.08 (d, 3H), 1.12 (d, 3H), 1.14-1.25 (m, 1H), 1.52-1.72 (m, 4H), 1.83-1.91 (m, 1H), 2.32-2.46 (m, 1H), 3.64-3.69 (m, 1H), 8.81 (s, 1H)

Reference Production Example 3-4

3.1 g of cis-2,6-dimethylcyclohexanoneoxime and 12 g of poly phosphoric acid were added to 40 ml of xylene and stirred at 100° C. for 10 hours. Then the reaction mixture which was cooled to about room temperature was added to ice-water. Potassium carbonate was added to it, and extracted with ethyl acetate three times. The organic layers were joined, washed with saturated aqueous solution of sodium chloride, dried with anhydrous magnesium sulfate, and concentrated. The residue was subjected to silica gel column chromatography to obtain 2.5 g of hexahydro-cis-3,7-dimethylazepin-2-one.

hexahydro-cis-3,7-dimethylazepin-2-one

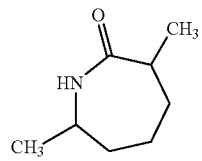

$^1$H-NMR: 1.31 (d, 3H), 1.91 (d, 3H), 1.26-1.36 (m, 1H), 1.40-1.51 (m, 1H), 1.60-1.76 (3H), 1.91-1.97 (m, 1H), 2.48-2.56 (m, 1H), 3.49-3.58 (m, 1H), 5.36 (brs, 1H)

Reference Production Example 3-5

0.54 g of lithium aluminum hydride was suspended to 20 ml of tetrahydrofuran, then 1 g of hexahydro-cis-3,7-dimethylazepin-2-one was slowly added to it at 0° C., further refluxed for 10 hours. The reaction mixture was cooled to 0° C.; and 0.54 ml of water, 0.54 ml of 15% aqueous solution of sodium hydroxide and 1.62 ml of water were added successively to it; then stirred for 30 minutes. Anhydrous magnesium sulfate was added to it and filtered through Celite®. 8.4 ml of hydrogen chloride-diethyl ether solution (1 mol/L) was added to the obtained filtrate at 0° C., and stirred for 1 hour. The mixture was concentrated to obtain 1 g of cis-2,6-dimethyl hexahydroazepin hydrochloride.

cis-2,6-dimethyl hexahydroazepin hydrochloride

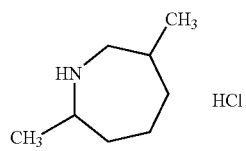

$^1$H-NMR: 1.01 (d, 3H), 1.21-1.33 (m, 1H), 1.48 (d, 3H), 1.60-1.72 (m, 2H), 1.79-2.01 (m, 3H), 2.12-2.21 (m, 1H), 2.77-2.88 (m, 1H), 3.22 (brd, 1H), 3.54 (brs, 1H), 9.44 (br, 2H)

Next, Reference Formulation Examples of the 4-amino-6-alkynyloxypyrimidine compound shown by the formula (V) are described. Parts are by weight.

Reference Formulation Example 1

Nine parts of each of the present compounds (1) to (10) is dissolved in 37.5 parts of xylene and 37.5 parts of N,N-dimethylformamide, and 10 parts of polyoxyethylene styryl phenyl ether and 6 parts of calcium dodecylbenzenesulfonate are added thereto, followed by well mixing with stirring, to give an emulsifiable concentrate for each compound.

Reference Formulation Example 2

Nine parts of each of the present compounds (1) to (10) is added to a mixture of 4 parts of sodium lauryl sulfate, 2 parts of calcium lignin sulfonate, 20 parts of synthetic hydrated silicon oxide fine powder, and 65 parts of diatomaceous earth, followed well mixing with stirring, to give a wettable powder for each compound.

Reference Formulation Example 3

Three parts of each of the present compounds (1) to (10), 5 parts of synthetic hydrated silicon oxide fine powder, 5 parts of sodium dodecylbenzenesulfonate, 30 parts of bentonite, and 57 parts of clay are well mixed with stirring, and an appropriate amount of water is added to the mixture of these ingredients, followed by further stirring, granulation with a granulator, and drying by ventilation, to give a granule for each compound.

Reference Formulation Example 4

First, 4.5 parts of each of the present compounds (1) to (10), 1 part of synthetic hydrated silicon oxide fine powder, 1 part of Doriresu B (available from Sankyo Co., Ltd.) as a flocculant, and 7 parts of clay are well mixed in a mortar and then mixed with stirring in a juicer. To the resulting mixture is added 86.5 parts by cut clay, followed by well mixing with stirring, to give a dust for each compound.

Reference Formulation Example 5

Ten parts of each of the present compounds (1) to (10), 35 parts of white carbon containing 50 parts of polyoxyethylene alkyl ether sulfate ammonium salt, and 55 parts of water are mixed and pulverized by wet grinding method to give a formulation for each compound.

Test Example shows that the 4-amino-6-alkynyloxypyrimidine compounds shown by the formula (V) produced by the production method of the present invention have pesticidal activity.

Test Example 1

A formulation of a test compound obtained in the Reference Formulation Example 5 was diluted with water so that the active ingredient concentration came to 500 ppm to prepare a test spray solution.

The seeds of cucumber were planted in polyethylene cups and grown until their first foliage leaves developed, on which about 20 cotton aphids (*Aphis gossypii*) were made parasitic. After one day, the test spray solution was sprayed at the rate of 20 ml/cup onto the cucumber plants. On the 6th day after the application, the number of cotton aphids was examined and the control value was determined by the following formula:

Control value(%)={1−($Cb$×$Tai$)/($Cai$×$Tb$)}×100 wherein the variables in the formula have the following meanings:
Cb: the number of insects before the treatment in the non-treated area;
Cai: the number of insects at the time of observation in the non-treated area;
Tb: the number of insects before the treatment in the treated area; and
Tai: the number of insects at the time of observation in the treated area.

As a result, in the treated area of the present compounds (1) to (7), the control value was 90% or higher.

Test Example 2

A formulation of a test compound obtained in the Reference Formulation Example 5 is diluted with water so that the active ingredient concentration come to 500 ppm to prepare a test spray solution.

The seeds of cabbage are planted in polyethylene cups and grown until their first foliage leaves developed. The first foliage leaves are left and the other leaves are cut off. Some adults of silverleaf whiteflies are set free on the cabbage plants and allowed to lay eggs for about 24 hours. The cabbage plants with about 80 to 100 eggs thus laid are left in a greenhouse for 8 days, and the above test spray solution is sprayed at the rate of 20 ml/cup onto the cabbage plants with larvae being hatched from the laid eggs. On the 7th day after the application, the number of surviving larvae is counted.

As a result, the cabbage leaves which test spray solution containing the present compound (1) to (10) is well controlled form pests.

INDUSTRIAL APPLICABILITY 4-amino-6-alkynyloxypyrimidine compounds shown by the formula (V) which has a controlling activity against pests can be produced by the production method of the present invention.

The invention claimed is:

1. A method for producing a 4-amino-6-alkynyloxypyrimidine compound shown by the formula (V):

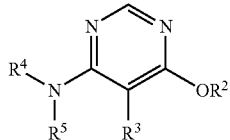
(V)

wherein $R^2$ represents C3 to C7 alkynyl, $R^3$ represents hydrogen or halogen, and $R^4$ and $R^5$ are combined together to represent C4 to C7 polymethylene and said polymethylene may be substituted by one or more groups selected from the group consisting of halogen, trifluoromethyl and C1 to C4 alkyl;
which comprises
the first step which produces a 4-fluoro-6-alkynyloxypyrimidine compound shown by the formula (I):

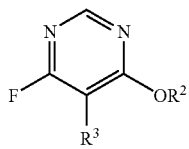
(I)

wherein $R^2$ and $R^3$ have the same meanings as described above,
by making a 4,6-difluoropyrimidine compound shown by the formula (II):

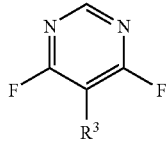
(II)

wherein $R^3$ has the same meaning as described above,
react with an alcohol compound shown by the formula (III):

 (III)

wherein $R^2$ has the same meaning as described above,
in the presence of a tertiary amine;
and the second step which produces the 4-amino-6-alkynyloxypyrimidine compound shown by the formula (V) by making the 4-fluoro-6-alkynyloxypyrimidine compound shown by the formula (I) react with an amine compound shown by the formula (IV):

(IV)

wherein $R^4$ and $R^5$ have the same meanings as described above.

2. The method for producing a 4-amino-6-alkynyloxypyrimidine compound shown by the formula (V) according to claim 1, wherein $R^2$ is 2-butynyl, $R^3$ is fluorine, and $R^4$ and $R^5$ are combined together to represent the group of formula —$CH_2CH(CH_3)CH_2CH(CH_3)CH_2$—.

3. The method for producing a 4-amino-6-alkynyloxypyrimidine compound shown by the formula (V) according to claim 1, wherein the tertiary amine is triethylamine.

4. A method for producing a 4-fluoro-6-alkynyloxypyrimidine compound shown by the formula (I):

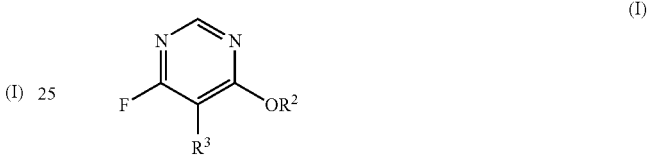
(I)

wherein $R^2$ represents C3 to C7 alkynyl, and $R^3$ represents hydrogen or halogen,
which comprises
the step making a 4,6-difluoropyrimidine compound shown by the formula (II):

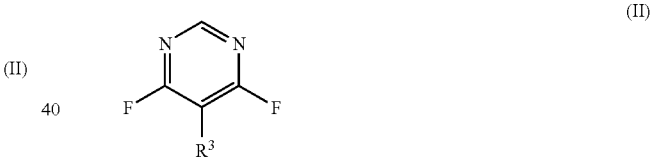
(II)

wherein $R^3$ has the same meaning as described above,
react with an alcohol compound shown by the formula (III):

 (III)

wherein $R^2$ has the same meaning as described above,
in the presence of a tertiary amine.

5. The method for producing a 4-fluoro-6-alkynyloxypyrimidine compound shown by the formula (I) according to claim 4, wherein $R^2$ is 2-butynyl, and $R^3$ is fluorine.

6. The method for producing a 4-fluoro-6-alkynyloxypyrimidine compound shown by the formula (I) according to claim 4, wherein the tertiary amine is triethyl amine.

* * * * *